United States Patent
Taylor et al.

[11] Patent Number: 5,828,458
[45] Date of Patent: Oct. 27, 1998

[54] TURBIDITY SENSOR

[75] Inventors: Robert E. Taylor, Cadillac; David W. Bull, Hersey, both of Mich.

[73] Assignee: Nartron Corporation, Reed City, Mich.

[21] Appl. No.: 381,267

[22] Filed: Jan. 26, 1995

[51] Int. Cl.⁶ .................................................. G01N 21/05
[52] U.S. Cl. ........................................ 356/440; 350/70
[58] Field of Search ....................................... 356/440, 70

[56] References Cited

U.S. PATENT DOCUMENTS

| | | | |
|---|---|---|---|
| 3,628,028 | 12/1971 | Thorsheim | 250/576 |
| 3,771,472 | 11/1973 | Stonner et al. | |
| 4,201,471 | 5/1980 | Pitt et al. | 356/70 |
| 4,265,535 | 5/1981 | Pitt | |
| 4,420,256 | 12/1983 | Fladda et al. | 356/336 |
| 4,601,082 | 7/1986 | Kurz | 15/319 |
| 4,801,204 | 1/1989 | Nakamura et al. | 356/338 |
| 4,874,243 | 10/1989 | Perren | 356/342 |
| 4,906,101 | 3/1990 | Lin et al. | 356/442 |
| 5,049,742 | 9/1991 | Hosonuma et al. | 356/70 X |
| 5,082,367 | 1/1992 | Kohler et al. | 356/73 |
| 5,102,550 | 4/1992 | Pizzino et al. | 210/640 |
| 5,104,228 | 4/1992 | Baillie | 356/442 |
| 5,147,560 | 9/1992 | Nichols | 210/745 |
| 5,173,190 | 12/1992 | Picek | 210/651 |
| 5,230,227 | 7/1993 | Kohdoh et al. | 68/12.02 |
| 5,241,368 | 8/1993 | Ponstingl et al. | 356/436 |
| 5,241,845 | 9/1993 | Ishibashi et al. | 68/12.02 |
| 5,245,200 | 9/1993 | Fladda | 356/336 |
| 5,259,219 | 11/1993 | Dausch et al. | 68/207 |
| 5,291,626 | 3/1994 | Molnar et al. | 68/12.02 |
| 5,303,029 | 4/1994 | Sioma et al. | 356/339 |
| 5,304,492 | 4/1994 | Klinkhammer | 436/52 |
| 5,341,661 | 8/1994 | Dausch et al. | 68/207 |

*Primary Examiner*—Vincent P. McGraw
*Attorney, Agent, or Firm*—Brooks & Kushman P.C.

[57] ABSTRACT

A fluid turbidity or filter clog sensor comprises a light source and a detector having at least one sensor position to cross a flow path or a filter element in order to improve the correspondence of the light intensity received at the receiver in correspondence with the turbidity level or clogging level occurring in the test cell. The detector preferably includes a direct path sensor, a scattered path sensor positioned to cross the flow path from the transmitter, and the reference light sensor communicating with the source outside of the test chamber. Moreover, the direct path may be a straight line path or a reflected path through the flow path when a fluid having a low level of turbidity is passed through the test cell. Likewise, the sensor includes means for compensating for changes in the illuminating source, changes for temperature variations occurring at the test cell, and compact packaging for convenient installation and improved production capacity.

22 Claims, 4 Drawing Sheets

TURBIDITY SENSOR

FIELD OF THE INVENTION

The present invention relates generally to a turbidity sensor for sensing the cloudiness or contamination level of a sample fluid that passes through a test cell or the clarity level of a filter.

BACKGROUND ART

Turbidity sensors monitor the status of a fluid and more particularly determine the presence or level of impurities in the fluid. Often the presence of impurities determines the suitability of the fluid for use in its intended purpose. As an example, lubricating oil having too high a contamination level should be cleansed or changed.

Certain prior art turbidity sensors operate by shining a light into a test cell that contains the fluid under scrutiny. The degree to which the light is transmitted as well as scattered gives an indication of the turbidity or pureness of the fluid sample. The previously known turbidity sensors often use light emitting diodes (LED's) for light sources and the use of photodiodes and phototransistors for use as detectors to reduce costs. An output from such systems may employ light intensity to frequency converters. For example, a photodiode or phototransistor that monitors light intensity is coupled to such a converter to generate a signal whose frequency corresponds to and varies with the turbidity level of the fluid.

A problem identified in prior art turbidity sensors is that the light source that shines light into the fluid sample can change its emission characteristics with time or with variations in temperature. Similarly, changes in operating characteristics can take place in the sensors that are used to sense the light that travels through the fluid.

Prior art turbidity sensors have experienced problems when trying to sense the condition of fluids that are either at low or high turbidity levels. In addition, the sensor's test cell must be large enough to pass all suspended particles in the test material without fouling. The test cell must also be small enough, however, to allow light to be transmitted through the cell and received by a sensor on the opposite side of test cell from the source. At high turbidity levels, a long transmission path will not pass enough light to allow the sensor to provide a meaningful measurement as the variation in light output such as a frequency. Conversely, at low turbidity levels, a test cell's transmission path may be too short to allow sufficient light to be scattered or absorbed to produce a meaningful measurement.

Many fluid filters for liquids and gases function by particle entrapment. As filters gradually become clogged by the particles, detection of the need for cleaning or replacement is often accomplished by mass air flow measurements downstream of the filter, pressure drop measurements across the filter and motor or pump loading. All of these techniques have disadvantages in terms of cost, accuracy or reliability.

In addition, the structure and assembly of previously known turbidity sensors is often complex, particularly where the structure supports for the components are arranged to avoid improper alignments of the components with respect to each other. As a result, any supports for the component that are adjustable so as to permit a final alignment of the parts after assembly are quite complex and costly. Moreover, the previously known components and the support structures for the components are not well adapted for simple and economical mass production, and the assembly of products employing turbidity sensors that otherwise would be readily mass produced can be substantially complicated by installation of the previously known support structures and component assemblies.

In addition, the performance of systems using light sensors can be substantially affected by temperature changes and component changes due to aging, contamination and the like.

DISCLOSURE OF THE INVENTION

The present invention overcomes the above disadvantages of the existing prior art turbidity sensors by providing a sensor that improves the accuracy of its output over a range of conditions and that can be packaged economically. The sensor can be used with a test cell through which a fluid flows or with a filter that filters sediments or contaminants from a fluid.

In general, a turbidity sensor constructed in accordance with the present invention includes structure that defines a flow path for a fluid and supports a light source that shines light through the path of the fluid. At least one light detector senses light that has passed through at least a portion of the fluid. Preferably, a first light detector measures transmitted light and a second light detector measures light that has been scattered by the fluid. A control circuit, preferably including a light-to-frequency converter, monitors first and second output signals from the first and second light detectors to generate an indication output of level of the turbidity of the fluid. In addition, improvements in the correspondence of the outputs to the turbidity level detectors are available in lieu of, or in addition to, the multiple or single detectors.

Improved correspondence between the sensor output and the turbidity can be provided by a compensation circuit that may include a third light detector located in a position to detect light directly transmitted from the source. A feedback circuit coupled between the third light detector and the light source controls the intensity of light output from the light source based upon the intensity of light reaching the third detector. Alternatively, a compensator improving the sensor output's correspondence to turbidity may include other sensors, such as a thermistor, to adjust the source intensity. Nevertheless, use of the feedback circuit allows the light output intensity from the source to be controlled so that the intensity is relatively constant even though conditions such as temperature in the region of the source change. Accordingly, a low cost, high performance sensor is provided without resort to a source different from the light emitting diodes used in the prior art.

In addition, the present invention provides a simple housing structure for accurately supporting components of the sensor in proper alignment for the sensing the turbidity of a medium between the source and the detector. In one preferred embodiment, the optical path between the source and the detector is defined as a straight line between an LED and the center of a light-to-frequency convertor photodiode array, and passing through the center of a quartz tube carrying a fluid medium. The test cell is carried within a housing, preferably made of two symmetrical parts, that preferably provides fluid inlets and outlets to the test cell that complies with the flow standards for an existing flow system such as a dishwashing appliance. An optical carrier in the form of a sleeve supports the detector on an optical axis across the medium. The electrical components, preferably arranged on a circuit board supported within the housing by the sleeve, are enclosed outside of the flow path. In another embodiment, the path is deflected from a circuit board carried by a housing. Molded in one piece with a tube, the reflectors defining the path through the tube.

BEST MODE FOR PRACTICING THE INVENTION

Figure 1:
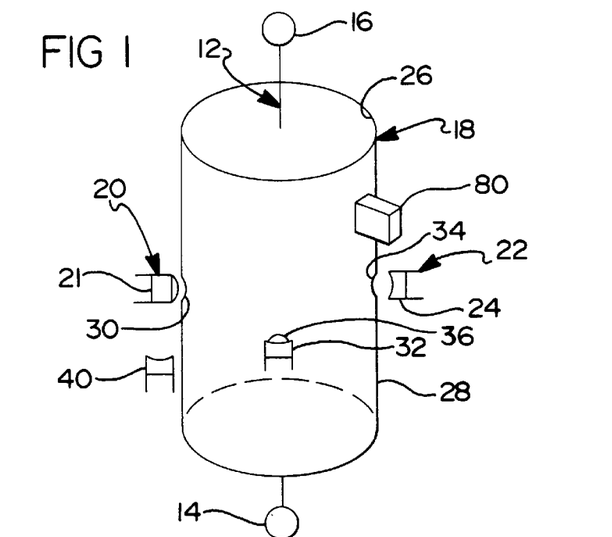
FIG. 1 is a schematic depiction of a turbidity sensor constructed in accordance with the present invention.

Referring first to FIG. 1, a turbidity sensor 10 senses the turbidity of a fluid flowing along a flow path 12, from a fluid source 14, such as a pump, to an outlet 16. A test cell 18 along the path 12 includes a light source 20, preferably an LED 21, and at least one detector 22, preferably comprising at least one photodiode 24. The photodiode 24 provides a light intensity output in the form of a current signal that can be converted by an operational amplifier to a voltage signal whose level is related to the light intensity received and inversely related to turbidity. In the preferred embodiment, the detector 22 also includes additional features to provide outputs that refine the sensor output for improving the output responses' correspondence to the turbidity level of the fluid in the flow path 12. The output responses are stored, preferably in RAM or in an EEPROM, or used, for example, in a control process to compare a reference fluid response with a response for a measured level of turbidity.

A turbidity sensor 10 constructed in accordance with the present invention can include a test cell chamber 26 having generally cylindrical side wall 28 with an opening 30 that transmits light generated by a source 20 positioned outside the test cell chamber 26. The disclosed test cell 26 defines a flow path portion that is generally circular in cross section and allows fluid to flow through the test cell chamber 26 for evaluation.

The illustrated sensor 22 of the preferred embodiment also includes photodiodes 24 and 32 for sensing light at positions separated from the source LED 20. A first photodiode 24 detects light that traverses across the test cell 26 and exits through an opening or unobstructed window 34 in the wall 28. The second photodiode 32 is also outside the test cell and is positioned at a window 36 aligned at an angular position between the LED 21 and the first photodiode 24. The second photodiode 32 detects light that enters the wall of the test cell but is scattered by the suspended material in the fluid.

Figure 2A:
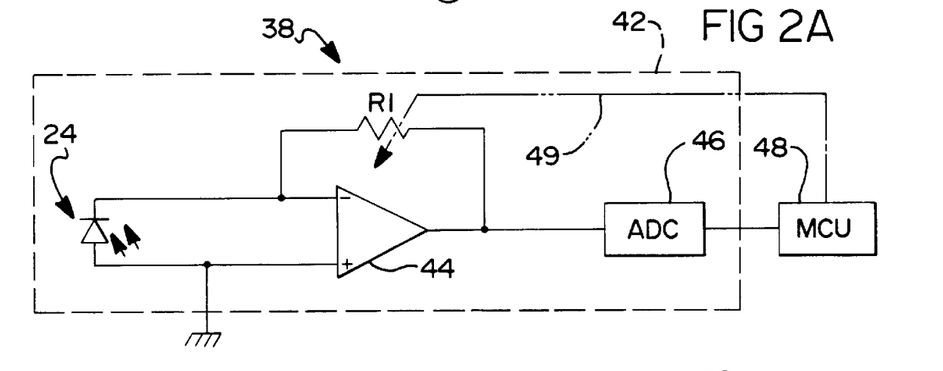
FIGS. 2A and 2B are schematic diagrams of circuits for monitoring outputs from two photodiode used as turbidity sensors and controls for driving an LED source respectively.

The photodetector 24 is coupled in monitoring circuit 38 as shown in FIG. 2A. When the detector comprises one or more photodiodes as previously discussed, each diode may be coupled in a detector circuit 42 that comprises a part of the monitoring circuit 38. For example, as specifically shown in FIG. 2A, the photodiode 24 is coupled as an input to an operational amplifier 44. Resistor R1 defines the gain of the operational amplifier 44. The output of the operational amplifier 44 is delivered to an analog-to-digital converter (ADC) 46 to provide a signal that can be used in the microcontroller unit (MCU) 48. The microprocessing control unit 48 may also provide useful input, for example, a gain control to the LED driver in order to adjust for the characteristics of different sensitive photodiodes 24, or different operating conditions or ranges of turbidity levels to be monitored by the circuit 38. Alternatively, the microprocessor can control gain of the detector circuit as shown at 49 in phantom line in FIG. 2A.

The detector circuit 42 may also be more conveniently provided by an alternative to conventional discrete, components and combinations of photodiodes as previously discussed. In particular, a light-to-frequency converter combines a photodiode and a high performance current-to-frequency converter circuit in a compact package. For example, a Texas Instruments TSL 235 light-to-frequency converter offers direct high-resolution conversion of light intensity to a readily read digital pulse format acceptable by the microprocessing controller unit 48. Such a detector provides a simple way to process a wide dynamic range of light levels with inexpensive microcontrollers, such as Microchip's PIC16CR54. The output of the light-to-frequency converter provides a frequency directly proportional to the light intensity on the photodiode. Such a converter is preferred because the device provides generally linear response over variations in temperature, often including temperature compensation, generally linear response throughout a wide frequency range.

Referring again to FIG. 1, in addition to the two photodiodes 24, 32, a third photodiode 40 monitors the strength of the light emanating from LED 21 of the source 20. The third photodiode 40 is positioned to intercept light from the LED source 20 outside of the test cell chamber 26 so that the light from the source can be sensed without interference or interaction with the test cell 22.

Figure 2B:
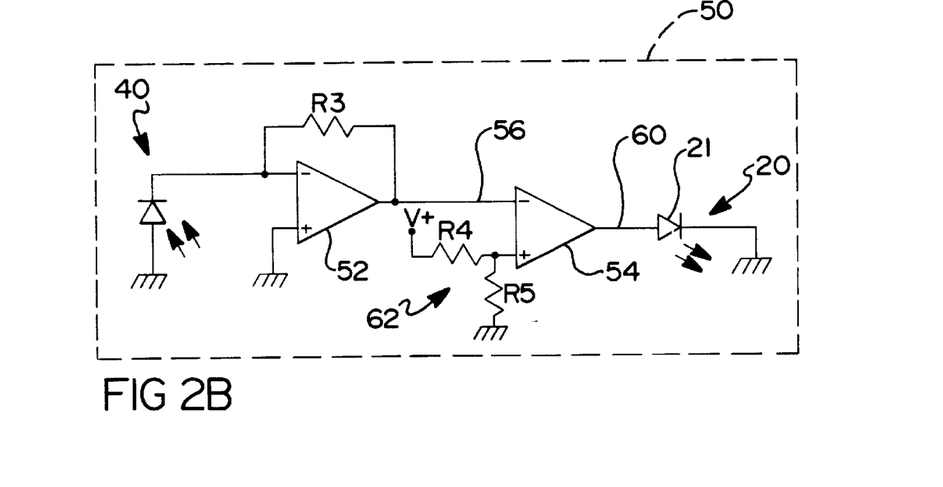

FIG. 2B is a schematic diagram of a circuit 50 that maintains a constant output from the source 20 to compensate for changes in light intensity that can occur over time. In this circuit 50, an output signal from the third photodiode 40 is compared to an external voltage reference at operational amplifier 54 that is also the output driver for the LED 21. The light output from the LED 21 then provides a negative feedback loop through photodiode 40 and its amplifier 52 to the input to the amplifier 54.

The size of the output from the operational amplifier 54 is controlled by two resistors R4, R5 that form a voltage divider 62. A reference voltage V+ defines the size of the voltage at the noninverting input to the amplifier 54.

Any drop in light output from the LED 21 sensed by photodiode 40 decreases the output signal from the first operational amplifier 52. Reduced output 56 increases the drive current from the output 60 of the second operational amplifier 54, and increases current through the LED 21. The negative feed back will continue until the light output from the LED 21 is sufficient to bring the voltage from the first operational amplifier 52 substantially equal to the signal provided by the voltage divider 62. Increases in light output from the LED 21 will result in a corresponding drop in drive current 60 until an equilibrium state is achieved.

Acoordingly, the circuit 50 provides a constant level of light output which is independent of LED output efficiency due to temperature changes or aging of the circuit, so that changes in output from the two other photodiodes 24 and 32 are more closely related to changes in the turbidity level.

With the disclosed circuit configurations, including constant LED output, the test cell can be evaluated by comparison of output response from operation whenever non-turbid material passes through it. With a nonturbid medium, any changes in scattered light that is detected at the photodiode 32 or changes in transmitted light at the photodiode 24 corresponds more closely to the contamination level of the test cell rather than the turbidity level of fluid within the test cell.

One type of monitoring process analyzes signal changes in the outputs from the photodiodes 24, 32 as readings beyond predetermined threshold values may be used to generate a failure indication. A perceptible indication output, such as a warning light or audible alarm, may warn of a need to clean or replace the test cell. In other applications, the monitoring process would signal actuation of a cleansing cycle that passes non-turbid fluid through the test cell until it is sufficiently clean. In cases where a degree of contamination of the test cell is acceptable or must be ignored, the outputs from the two photodiodes 24, 32 are used as references for ratiometric and/or differential comparisons in the microprocessor 48, for example, compare a reading for the fluid under test with a reading for a reference fluid of known turbidity.

An additional refinement of the present invention shown in FIG. 1 is that the wall 28 of the test cell supports a temperature sensor 80. Regardless of the placement of the temperature sensor 80, it measures temperature of the test cell 18 or the temperature of the fluid within the cylindrical wall 28 of the test cell 18, to provide an adjustment of detector output or provide a fluid temperature signal for other functions such as a temperature read-out or display. The sensor 80 can be an infrared sensor or other known type, but is preferably, a thermistor, that changes resistance as temperature variations occur. A signal from the sensor 80 can be used to facilitate any needed temperature corrections to the outputs of the three photodiodes 24, 32, 40 in the processing of the photodiode outputs in the microprocessor 48.

Figure 3:
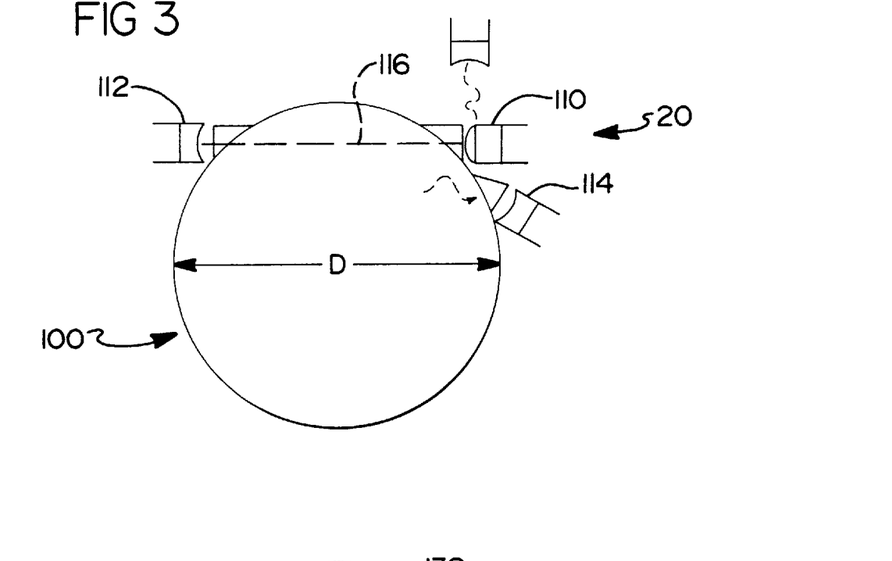
FIG. 3 is an alternate test cell design for use with highly turbid fluids.

When a large amount of suspended material is in the fluids to be tested, a large diameter test cell will prevent fouling of the test cell. However, a large diameter test cell can be a problem because a long optical transmission path for extremely turbid fluid such as dirty water, or for optically absorptive material such as dirty motor oil, may not provide an adequate range of light transmissibility to the range of turbidity levels encountered. As shown in FIG. 3, a test cell 100 having a relatively large diameter D supports a source 20 such as LED 110 and detector 22 such as the direct sensing photodiode 112 along a short chord path 116 to shorten the sensing distance, and the scattered light detector photodiode 114 facing the flow path.

Figure 4:
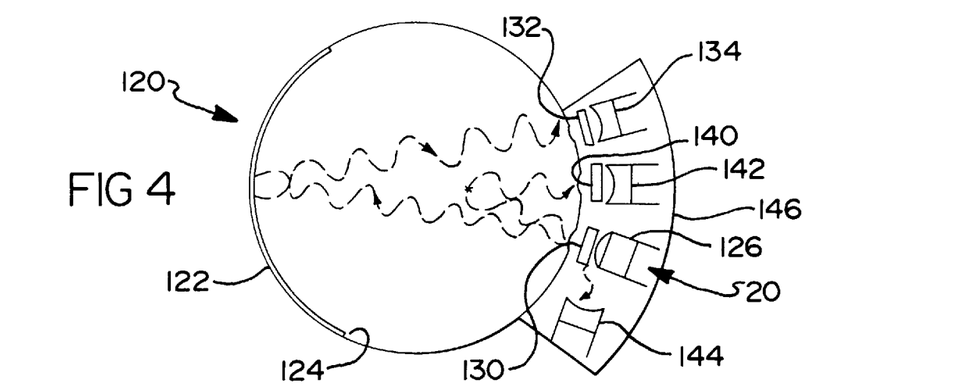
FIG. 4 is an additional alternate test cell design for use with low turbidity fluids.

When the turbidity level is low, the optical path length through the medium under test may be increased to improve performance. However, increasing the diameter of the test cell has practical limitations, particularly those based on the volume of fluid per unit time flowing through the system. As shown in FIG. 4, a reflective surface 122 is formed on the inside wall 124 of the test cell 120. A source 20 comprising LED 126 is positioned outside the test cell to direct light through an optical path. An optical path may include a lens and/or an aperture stop 130 that limits the angle of light rays transmitted. Accordingly, light transmitted from the source 126 reflects off the reflective surface 122 and bounces back to an aperture stop or lens 132 that allows reflected light to reach a first photodiode 134. A lens or aperture stop 140, such as an opening offset from the center of a second photodiode, directs scattered light from the medium to the second photodiode 142 while blocking light from the reflective surface 122 of the test cell. A third reference photodiode 144 is located to receive light directly from the source LED 126. A further advantage of this design using a reflective light path length is that it reduces the size of the test cell, and simplifies packaging of all the photodiodes in a single housing 146 next to the test cell 120.

A large concentration of small particles would have an averaging effect which would be expected to affect the signal(s) in a slowly varying manner. However, a lower concentration of large particles would tend to cause rapid fluctuations as large particles individually blocked large portions of the transmission optical path or momentarily presented large scattering surfaces to reflect light into a scattered light sensor. High pass filters would indicate presence of the large particle signals whereas low pass filters would tend to average the effect of all particles, large or small. By applying low and high pass filters separately on both a transmission and a reflection sensor, the following logic could be used.

A drop in signal from the low pass filtered transmission detector (LPT), an increase in signal from the low pass filtered reflection sensor (LPR) and a small signal from the high pass filtered transmission (HPT) and reflection (HPR) sensors would indicate the presence of a concentration of small or dissolved particles. Little or no signal from the LPT, HPT and HPR would indicate a large concentration of particles in the tested medium. A drop in the LPT, increase in LPR and a signal from both the HPR and HPT would indicate the presence of large particles. Little or no signal from the LPT and HPT with signals from the LPR and HPR would indicate the presence of large particles or the presence of large particles in a very turbulent medium.

A detector located to receive scattered radiation "S" as at 32 in FIG. 1 and another is located to receive transmitted radiation "T" as at 24 in FIG. 1 and both signals are both input to a high pass filter and a low pass filter. In other words, a large high pass filtered "S" would indicate the presence of larger particles that intermittently present scattering surfaces to the emitted light. A small high pass filtered "S" would indicate a lack of larger scattering particles. A large low pass filtered "S" would indicate the presence of a steady stream of smaller scattering particles each of which provides a small reflecting surface and together provide a slowly varying total amount of reflected light. A small low pass filtered "S" would indicate isolated or few particles.

A large high pass filtered "T" would indicate the presence of a low concentration of large particles that intermittently completely block the transmission path while leaving it clear the rest of the time. A small high pass filtered "T" would indicate a high turbidity that could be large or small particles, or a low turbidity of fairly evenly distributed small particles. A large low pass filtered "T" would indicate a low turbidity level. A small low pass filtered "T" would indicate a high turbidity of large or small particles.

This type of logic would be useful in measuring the degree of mixing in a solution where it is necessary to dissolve or break up large particles. It could also be useful in determining the nature of the contamination in a medium.

In a dissipative media, the relationship between the path length "x" and the transmitted intensity "T" is given by the equation:

$$T = T_0 \cdot e^{-\lambda \cdot x} \quad (1)$$

In this equation, the coefficient of absorption λ is a factor of the turbidity. The larger λ is, the greater the rate of absorption with respect to path length and correspondingly, the greater the turbidity. In cases where the turbidity is due more to scattering than to absorption, the relationship between transmission and path length may not be strictly exponential, since some light scattered away from the path to a detector could rescatter back to a path to the detector. However, the fraction of unscattered light at any given path length, would be expected to be exponential with respect to path length.

For an exponential dependence on "T", the transmission measured by two detectors through separate path lengths of $x_1$ and $x_2$, would be given by equation:

$$T_1 = T_0 \cdot e^{-\lambda \cdot x_1}$$

$$T_2 = T_0 \cdot e^{-\lambda \cdot x_2} \quad (2)$$

The detector output could be input to logarithmic amplifier followed by a differential amplifier to provide the output as shown in equation:

$$\ln(T_1) = \ln(T_0) = \lambda \cdot x_1 \quad (3)$$

$$\ln(T_2) = \ln(T_0) = \lambda \cdot x_2$$

$$\ln(T_2) = \ln(T_1) = \lambda \cdot (x_1 - x_2)$$

As can be seen, if $x_1$ and $x_2$ remain constant, the difference of the logs depends only on λ and not the emission strength ($T_0$) Differences due to detector efficiency and path geometry would appear as is multiplicative corrections in equation 2 and result in additive constant corrections in equation 3.

In some cases the system may have to operate in the presence of artificial lighting (generally this light varies at 120 Hz.) or natural light (generally this light provides a DC background). It is standard practice to eliminate these backgrounds by operating in an AC mode, generally at frequencies at least 1 or 2 orders of magnitude above 120 Hz. In this way the signal can be high pass filtered, for example, at say 500 Hz to eliminate the 120 Hz and DC backgrounds from artificial and/or natural light sources. The high pass filtered signal is then demodulated by rectification or peak detection (among other means) and then low pass filtered to recover the variation induced in the LED's (or other intended sources) light transmission and/or reflection, which could be at or below 120 Hz.

Another embodiment would be to use two transmission receivers at different distances. Absorption is generally exponential in its relationship to distance. The ratio of the signals from the two receivers would allow the absorption coefficient and hence the turbidity to be determined, independent of the amount of light from the LED. If logarithmic amplifiers were used, then a differential amplifier could compare their results and provide an output signal directly proportional to the absorption coefficient λ that correlates to turbidity level.

Figure 5:
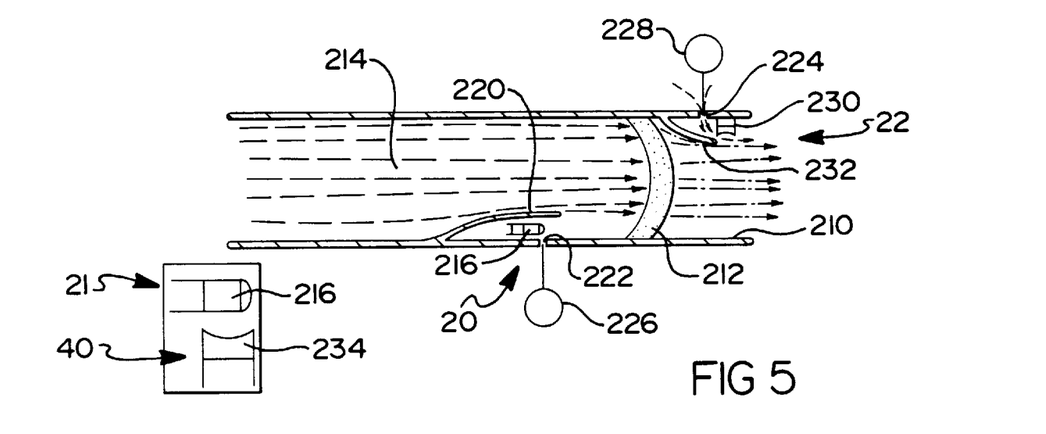
FIG. 5 discloses sensors for use in evaluating a filter condition.

Referring now to FIG. 5, the invention is applied to a filter chamber 210 containing a filter 212. A medium 214 containing contaminants or particles enters the filter chamber 210 upstream of the filter element 212. The medium passes through the filter 212 as the suspended particles are removed from the medium, and the filtered medium exits the filter chamber downstream of the filter 212. A light emitting source 20 such as a diode LED 216 is positioned within a baffle 220 to illuminate the filter. The baffle 220 deflects the medium away from the LED to minimize coating of the LED by contaminants in the medium 214. Alternatively, a source 20 combining a source intensity detector 40 as shown at 216 and a source LED 21 as shown at 234 encased in protective covering such as glass may be installed. Moreover, the combination may be installed within the baffle 220 or the enclosure may be shaped like the baffle.

A detector 22 such as photodiode 230 is positioned downstream of the filter 212 behind a second baffle 232 to detect light transmitted through the filter 212. As the particle laden medium strikes the filter 212, the pores of the filter will become progressively blocked by entrapped particles and additional particles may be layered on the upstream surface of the filter. These particles absorb or scatter light to divert the light from the photodiode 230. When the filter is clogged or blocked, the amount of light detected by the photodiode falls below a predetermined level. Alternatively, failure to reach a minimum signal level from the reference photodiode 216 may be used as an indication of the light source 20 having become covered by particles or suffering an operation failure.

As with the previously described turbidity sensors, a reference photodiode 234 positioned within the baffle 220 to receive light directly from the LED can provide output used as feedback to the LED driver electronics to maintain a constant light output. In addition, an electrostatic charge is preferably applied on the baffles to keep small suspended particles away from the vicinity of the diodes.

Preferably, the baffles 220 and 232 are shaped to direct the moving media around the diodes. The shapes of the baffles 250, 252 are preferably chosen to improve the flow of the medium away from the diodes. For example, increasing the speed of the media over the surface of the baffles, may improve the flow away from the chamber side surface of the baffle, particularly where a lower pressure region will be created within the baffles to draw fluid from a port 222 or port 224. This in turn can draw a source 226 or 228, respectively, of particle free medium into the filter chamber through the ports and over the diodes to prevent them from becoming covered by particles. The sources can be pressurized or non-pressurized external fluids or even medium flow in a loop from downstream of the filter.

Of course, cleaning of the source 20 and detector 22 can occur by passing another medium for cleansing of the test cell, for example, a fluid from a filtered or pressurized source of clean fluid. For example, in a dishwasher flow system, the last rinse cycle may be used to flush the system and prepare it for a subsequent wash cycle. In addition, the last rinse cycle may be used to take a reference reading or the detector response. The reference reading is stored for use in the microprocessor, for example, comparison with an original clear water cycle, to determine the degree of deterioration in the components of the detector or as a new reference value that represents a new value for comparison so that the comparison adjusts for use of the cell and other components.

Figures 6, 7:
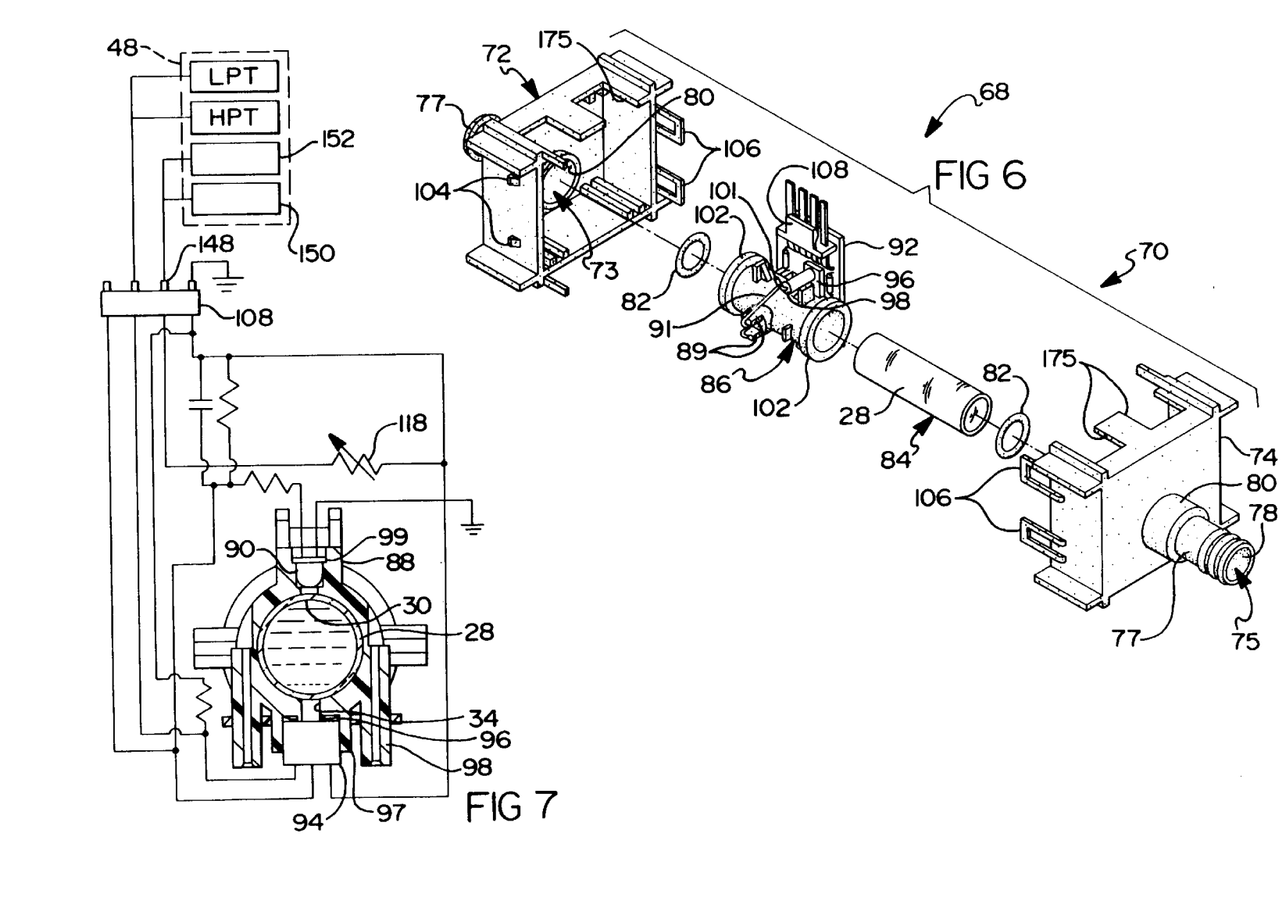
FIG. 6 is an exploded, perspective view of a preferred housing package for an embodiment of the present invention.
FIG. 7 is a schematic diagram of a circuit employed in the housing package of FIG. 6.

Referring now to FIG. 6, a housing 70 is shown comprising two halves 72 and 74 preferably constructed identically the same for production and assembly efficiency. Housing part 72 and housing part 74 include the input 73 and outlet 75, respectively, for the test cell package 68. The inlet 73, as well as the outlet 75, includes a fluid conduit coupling sleeve 77 externally ribbed for fluid-tight engagement with flexible conduit hose. The interior wall 78 of the coupling sleeve 77 tapers diametrically inward toward the interior end of the sleeve where the sleeve 77 meets with a socket recess 80.

Socket recess 80 receives an O-ring 82 having an inner diameter opening adapted to receive a quartz tube 84, for example quartz type 214, forming a test cell wall 28.

The quartz tube 84 is received in an optical carrier support sleeve 86 containing side wall openings 30 (FIG. 7) and 34 (FIG. 7) for a source 20 (FIG. 1), for example, a red light emitting Marktech MT 7203 UR diode, and a detector 22 (FIG. 1), for example, a Texas Instruments TSLC 102, respectively. A boss 88 (FIG. 7) surrounds the opening 30 and carries support fingers 89 adapted to carry the wire conductors 91 of the transmitter LED 90. Diametrically opposed to the boss 88, the optical carrier support sleeve 86 is adapted to contain a circuit board 92 adapted to hold the receiver IC 94 (FIG. 7), such as a Texas Instruments TSL 235 or TSL 230, over the receiver aperture 34 (FIG. 7). The carrier 86 includes alignment fingers 97 for the IC 94 and the IC 94 is prealigned on the circuit board, to ease assembly. Likewise, abutment surfaces 99 on the carrier 86 align the LED 21 for proper alignment on the optical path.

An apertured foam gasket 96 made of closed cell neoprene rubber excludes environmental contamination or light and is supported by a pair of hollow poles 98 (FIG. 6). The aperture in the gasket is defined by a peripheral wall that surrounds the opening 34 between the sleeve 86 and receiver IC 94. The poles 98 carry conductor 101 having one end soldered to the circuit board 92 and the other end soldered to the conductors 91 carrying the transmitter LED 90. Each end of the sleeve 86 includes a radially enlarged flange 102 that can be pressed against the side of the O-ring 82, to press it tightly in sealing engagement with the quartz tube 84 and the peripheral wall of the socket 80. The O-ring also allows differential expansion between the tube and the plastic housing.

The housing halves 72 and 74 are held together by ramp projections 104 engaging the slots in slotted fingers 106 to form snap connectors 103. The halves 72 and 74 also form openings 175 that enable a conductor terminal 108 to be exposed for a connection exterior of the housing. The housing parts 72 and 74, like the carrier sleeve 86, may be injection molded or otherwise formed of plastic material for similar thermoexpansion and chemical resistance properties for the environmental conditions, for example, A50LA31 Cellon for a dishwasher flow circuit.

As best shown in FIG. 7, the circuit board 92 (FIG. 6) also carries the detection circuit, including temperature sensor 118, preferably including a thermistor, that senses the temperature of the interior of the housing 70, which temperature is primarily controlled by the temperature of the fluid flowing through the test cell enclosed within the housing.

The temperature sensor 118 generates an output signal through the terminal 148 of terminal coupling 108. The input may be fed directly into a microprocessor 48 for pertinent processing related to operation or condition indication displays that may be useful. In particular, a temperature sensor 118 may be used in the compensation circuit to compensate for turbidity changes due to temperature changes of the medium flowing through the turbidity sensor, as shown diagrammatically at 150. In addition, it may useful to provide a mere indication of the temperature being sensed in the fluid media even outside the processing occurring in the microprocessing unit 48. For example, an indicator 152 shown diagramatically in FIG. 7. For example, in a dishwasher, the temperature level at which the insoluble fats dissolve should be reached during the cleaning cycle, in order to assure that fats or oils are dissolved or removed from the dishes. Similarly the processor could be used in conjunction with the detector 150 to operate a hot water source or continue an additional wash cycle in order to assure the removal of fats and oil accumulated on the dishes.

Figure 8:
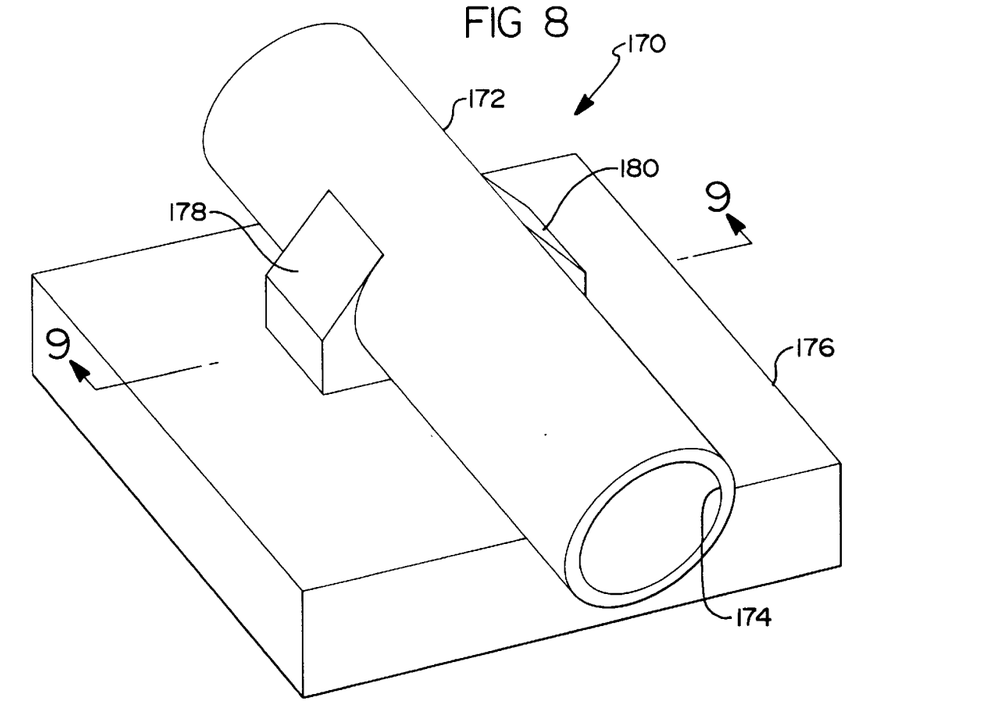
FIG. 8 is a perspective view of another preferred housing package for an embodiment according to the present invention.
Figure 9:
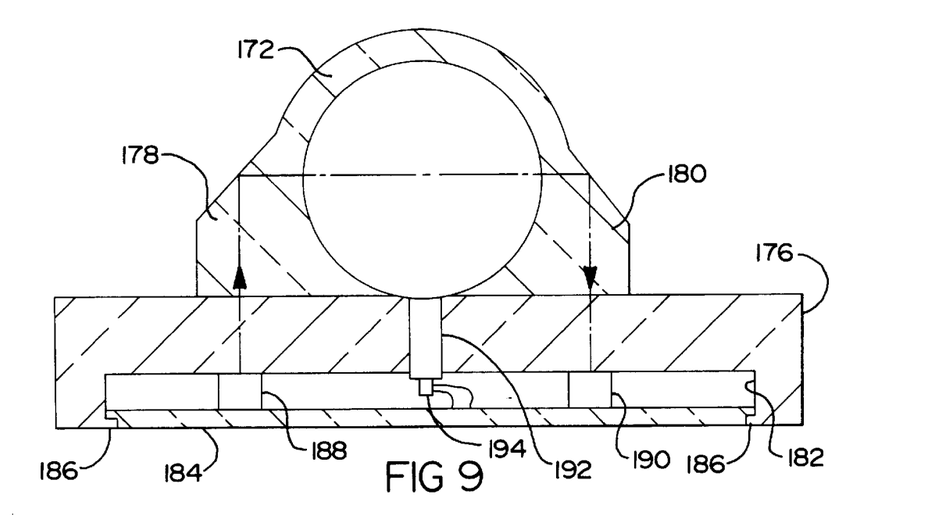
FIG. 9 is a sectional view taken substantially along the line 9—9 in FIG. 8.

Referring now to FIG. 8, another housing 170 is thereshown comprising a tube 172 with a central bore 174, the two being molded in one piece with a housing body 176 and two optical deflectors 178 and 180 that define an optical path across the tube 172. As best shown in FIG. 9, the bottom body 176 includes a recess 182 adapted to receive a circuit board 184. A circuit board 184 is retained in the cavity 182 by tabs 186 engaged in detents in the circuit board to retain the circuit board within the housing cavity.

The circuit board 184 carries an LED 188 in a position to direct light transmission through the housing to the deflector 178 across the test cell formed by the bore 174 and the tube 172. The optical path through the tube 172 then meets the deflector 180 where the optical path is directed downwardly to a photo detector 190 carried upon the circuit board 184. The important components in the optical path are aligned accurately automatically during construction, for example, by circuit board assembly apparatus and need not be manually aligned later.

An aluminum rod 192 is insert molded into the plastic body 176. The aluminum rod 192 is exposed to the cavity 182 for placement of a thermistor 194 in engagement with the aluminum rod for introduction of a temperature responsive signal to the detector circuit on the circuit board 184.

As a result, the present invention provides a simply installed test cell sensor housing which can be conveniently secured, by hose clamps or like, within a fluid system. In addition, the electrical connections to the light intensity-to-frequency converter may be readily coupled to a microcontroller for analysis of the transmitter, detector or reference signals which may be generated within the sensor's test cell housing. Moreover, the packaging is compact and readily produced by mass production techniques. Accordingly, the circuits, assembly and the physical features of the enclosure provide significant cost advantages in the production and assembly of turbidity sensors according to the present invention.

Having thus described the present invention, many modifications thereto will become apparent to those skilled in the art to which it pertains without departing from the scope and spirit of the present invention as defined in the appended claims.

What is claimed is:

1. A turbidity sensor for use in testing the condition of a fluid comprising:
   a) a test cell that defines a flow path through the test cell for a sample fluid to be sensed;
   b) a light source for shining light through the test cell as fluid under test flows through the test cell;
   c) first and second light detectors for sensing light that has passed through at least a portion of the fluid within the test cell wherein a first light detector measures transmitted light and the second light detector measures light that has been scattered by the fluid within the test cell;
   d) a third light detector located outside the test cell for calibrating the light source by detecting light transmitted from the source to the third light detector;
   e) a monitoring circuit for monitoring first and second output signals from the first and second light detectors to determine the turbidity of the fluid;
   f) a feedback circuit coupled between the third light detector and the light source for controlling the intensity of light output from the light source based upon the intensity of light reaching the third detector to maintain the light output intensity from said source due to varying conditions;

g) a temperature sensor attached to the test cell for monitoring a temperature and said monitoring circuit includes a compensation circuit that adjusts the indicated light intensity from the first and second light detectors based on sensed temperature;

h) wherein said first and second light detectors each generate a signal output corresponding to the light measurement, and further comprising a particle analyzer; and i) wherein said particle analyzer comprises a high pass filter coupled to the signal output of at least one of said first and second detectors, and a low pass filter coupled to said signal output of said at least one of said first and second detectors.

2. The turbidity sensor of claim 1 wherein the feedback circuit comprises a power amplifier to increase a signal from the third light detector and wherein the circuit further comprises a comparator coupled to the output of the power amplifier to compare the amplified signal from the power amplifier with a reference signal and adjust the light output from the source to maintain the amplified signal and the reference signal the same to provide uniform source intensity.

3. The invention as defined in claim 1 wherein said particle analyzer comprises a high pass filter coupled to the signal output of each of said first and second detectors, and a low pass filter coupled to said signal output of said at least one of said first and second detectors.

4. A method of testing the condition of a fluid by passing the fluid through a test cell that defines a flow path comprising the steps of:

a) shining light through the test cell as fluid under test flows through the test cell;

b) sensing light intensity of light passing through at least a portion of the fluid within the test cell wherein a first light intensity measurement measures transmitted light and a second light intensity measurement measures light that has been scattered by the fluid within the test cell;

c) calibrating the light source by detecting light transmitted from the source to a calibration light detector outside the test cell;

d) monitoring first and second light intensity signals from light detectors monitoring the scattered and transmitted light to determine the turbidity of the fluid;

e) controlling the intensity of light output from the light source based upon the intensity of light reaching the calibration detector to maintain the light output intensity from said source due to varying conditions including sensing temperature at said test cell and compensating for light intensity changes in response to said sensed temperature; and f) wherein said monitoring step comprises filtering said first and second light intensity signals in a first respective path having a high pass filter and filtering said first and second light intensity signal in a second respective path through a low pass filter to determine the size and number of particles in the fluid.

5. A compact turbidity sensor assembly for use in sensing the amount of suspended particles in a fluid, the sensor assembly comprising:

a body having a bore portion forming a passageway for conveying the fluid through the sensor assembly and configured to define a light emitter alignment surface and a light receiver alignment surface in an optical path through the passageway;

a light emitter aligned in the optical path by engagement with the light emitter alignment surface;

at least one light receiver aligned with the optical path by engagement with the light receiver alignment surface;

a circuit board having an electrical conductor for completing an electrical circuit with the light emitter and the at least one light receiver; and the body being configured to cooperate with at least one of the circuit board and the electrical conductor to position at least one of the light emitter and the at least one light receiver into engagement with its respective alignment surface and to position the circuit board in juxtaposition with the bore portion.

6. The compact turbidity sensor assembly as recited in claim 5 wherein the optical path between the light emitter alignment surface and the light receiver alignment surface includes at least one deflecting surface.

7. The compact turbidity sensor assembly as recited in claim 6 wherein the light emitter and the light receiver are contained in a cavity of the body remote from said passageway and containing the light emitter alignment surface and the light receiver alignment surface, respectively.

8. The compact turbidity sensor assembly as recited in claim 5 wherein the body is molded in one piece.

9. The compact turbidity sensor assembly as recited in claim 5 wherein the at least one of the light emitter and the at least one light receiver is mounted on the circuit board.

10. The compact turbidity sensor assembly as recited in claim 5 wherein the electrical conductor is formed by conductor portions connectable with each other after the circuit board is positioned in juxtaposition with the bore portion to complete the electrical circuit and retain in position the light emitter, the at least one light receiver, and the circuit board.

11. The invention as defined in claim 6 wherein said body defines said optical path with at least one deflecting surface angled to redirect light through said body back to said board.

12. The invention as defined in claim 11 wherein said light emitter and at least one said light receiver are mounted on a single board.

13. The invention as defined in claim 6 wherein both said light emitter and said at least one light receiver are mounted on a single circuit board and said at least one deflecting surface redirects said optical path to said circuit board.

14. A compact turbidity sensor assembly for use in sensing the amount of suspended particles in a fluid, the sensor assembly comprising:

a hollow carrier sleeve having at least two openings defining an optical path through the hollow, a light emitter for emitting light through the fluid and being supported by the hollow carrier sleeve in a first opening of at least two openings and at least one light receiver for receiving the emitted light and being supported by the hollow carrier sleeve in a second opening of the at least two openings;

a fluid tube slidably received in the hollow of the carrier sleeve in the optical path between the light emitter and the at least one light receiver for conveying the fluid past the light emitter and the at least one light receiver;

a pair of housing halves sandwiching the hollow carrier sleeve therebetween, each housing half including a coupling sleeve having one end for communicating the fluid respectively to or from the sensor assembly and another end for receiving a respective end of the fluid tube; and a sealing ring between each other end of each coupling sleeve and the respective end of the fluid tube for sealing the fluid in the fluid tube and sufficiently resilient to allow for differential expansion between the fluid tube and the housing halves.

15. The compact turbidity sensor assembly as recited in claim 14 wherein the housing halves are substantially identical.

16. The compact turbidity sensor assembly as recited in claim 14 including a circuit board supported on the hollow carrier sleeve.

17. The compact turbidity sensor assembly as recited in claim 16 wherein the housing halves include complementary notches which cooperate for receiving and exposing the circuit board for electrical connection outside the sensor assembly.

18. The compact turbidity sensor assembly as recited in claim 14 wherein the fluid tube is quartz.

19. The compact turbidity sensor assembly as recited in claim 14 wherein the housing halves include complementary latch means to connect the housing halves together.

20. The compact turbidity sensor assembly as recited in claim 19 wherein the latch means includes complementary slotted fingers and ramp portions to snap-fit the housing halves together.

21. The compact turbidity sensor assembly as recited in claim 16 wherein the circuit board includes an electrical conductor and the hollow carrier sleeve includes a guide post for locating a circuit board with respect to the hollow carrier sleeve and for receiving and directing the electrical conductor from the circuit board to the light emitter.

22. The compact turbidity sensor assembly as recited in claim 16 including a gasket in sandwiched relationship between the circuit board and the hollow carrier sleeve at the second opening on the hollow carrier sleeve to seal the at least one light receiver in the optical path.

* * * * *